US00PP25203P3

(12) United States Plant Patent
Doguet et al.

(10) Patent No.: US PP25,203 P3
(45) Date of Patent: Dec. 30, 2014

(54) *ZOYSIA*GRASS PLANT NAMED 'L1F'

(50) Latin Name: ***Zoysia japonica* (L.) Merr.**
Varietal Denomination: L1F

(71) Applicants: David Doguet, Pleasanton, TX (US); Virginia Lehman, Lebanon, OR (US)

(72) Inventors: David Doguet, Pleasanton, TX (US); Virginia Lehman, Lebanon, OR (US)

( * ) Notice: Subject to any disclaimer, the term of this patent is extended or adjusted under 35 U.S.C. 154(b) by 0 days.

(21) Appl. No.: 13/986,247

(22) Filed: Apr. 16, 2013

(65) Prior Publication Data

US 2014/0310842 P1 Oct. 16, 2014

(51) Int. Cl.
*A01H 5/00* (2006.01)

(52) U.S. Cl.
USPC ..... Plt./390

(58) Field of Classification Search
CPC ..... A01H 5/00
USPC ..... Plt./390
See application file for complete search history.

(56) References Cited

U.S. PATENT DOCUMENTS

| | | | | | |
|---|---|---|---|---|---|
| PP10,636 | P | * | 10/1998 | Engelke | Plt./390 |
| PP10,778 | P | * | 2/1999 | Engelke | Plt./390 |
| PP11,515 | P | * | 9/2000 | Engelke | Plt./390 |
| PP11,570 | P | * | 10/2000 | Engelke | Plt./390 |
| PP14,130 | P2 | * | 9/2003 | Engelke et al. | Plt./390 |

OTHER PUBLICATIONS

The Turfgrass Group, Inc, Oct. 2012, p. 14.*

* cited by examiner

*Primary Examiner* — June Hwu
*Assistant Examiner* — Keith Robinson

(57) ABSTRACT

An asexually reproduced variety of perennial zoysiagrass with a unique combination of morphological characters including medium to fine leaf blade width, low canopy height, and soft leaf texture.

2 Drawing Sheets

Latin name of the genus and species of the plant claimed: The present invention relates to the genus and species *Zoysia japonica* (L.) Merr.

Variety denomination: 'L1F'.

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

1. Field of Invention

The present invention relates to a new and distinct asexually reproduced variety of perennial zoysiagrass (*Zoysia japonica* (L.)) Merr.

BRIEF SUMMARY OF THE INVENTION

This invention relates to a new and distinct perennial zoysiagrass cultivar identified as 'L1F' zoysiagrass (herein referred to as 'L1F'). The inventors, David L. Doguet and Virginia G. Lehman, discovered 'L1F' under cultivated conditions near Poteet, Tex. in a collection of unknown plants from Kobe, Japan made by Jack Murray (deceased). 'L1F' was identified as a distinctly different vegetative patch or clonal plant differing from the surrounding plants in a medium to fine leaf texture, sparse flowering, and a rapid lateral growth rate. The inventors asexually reproduced 'L1F' by taking vegetative cuttings of stolons and rhizomes, cutting the rhizomes and stolons into segments, each with a vegetative bud, and rooting them in potting media. 'L1F' zoysiagrass will be used as a turfgrass suitable for home lawns, sports fields, and golf courses.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is zoysiagrass plant named 'L1F'.

BRIEF DESCRIPTIONS OF THE ILLUSTRATIONS

FIG. 1. Tiller of 'L1F' zoysiagrass.
FIG. 2. Inflorescence of 'L1F' zoysiagrass.

COMPLETE BOTANICAL DESCRIPTION OF THE VARIETY

'L1F' was characterized in greenhouse and field conditions. 'L1F' is a unique variety of zoysiagrass (*Zoysia japonica* (L.)) Merr. that was discovered under cultivated conditions. The inventors, David L. Doguet and Virginia G. Lehman, discovered 'L1F' in a collection of plants from Kobe, Japan made by Jack Murray (deceased) that was planted near Poteet, Tex. in 1998. 'L1F' was identified as a distinctly different vegetative patch or clonal plant differing from the surrounding plants in a medium to fine leaf texture, sparse flowering, and a rapid lateral growth rate. The plants were located in USDA Plant Hardiness Zone 8. The inventors asexually reproduced 'L1F' in both Poteet, Tex. and Lebanon, Oreg. by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'L1F' has been propagated by rhizomes, stolons, tillers, and sod. Asexually reproduced plants of 'L1F' have remained stable and true to type through successive generations of propagation. No seedling establishment from 'L1F' has been noticed in either greenhouse or field studies.

'L1F' is a perennial zoysiagrass that spreads by both stolons and rhizomes. Characteristics of 'L1F' measured in 2013 were taken from plants that were approximately 12 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'L1F' has a medium-fine leaf texture with a leaf length longer than 'Diamond' (U.S. Plant Pat. No. 10,636) but shorter than 'Cavalier' (U.S. Plant Pat. No. 10,778) and 'Zorro' (U.S. Plant Pat. No. 14,130) (Table 1). 'L1F' has an absence of leaf hairs versus 'Palisades' (U.S. Plant Pat. No. 11,515), 'Zorro' (U.S. Plant Pat. No. 14,130), 'Crowne' (U.S. Plant Pat. No. 11,570), and 'Cavalier' (U.S. Plant Pat. No. 10,778) which each have many leaf surface hairs (Table 2). 'L1F' has a thicker youngest stolon node and longer stolon internode lengths than 'Diamond' (U.S. Plant Pat. No. 10,636) (Table 3). 'L1F' has a shorter unmown canopy height than 'Cavalier' (U.S. Plant Pat. No. 10,778) or 'Zorro' (U.S. Plant Pat. No. 14,130) (Table 4), but lacks the winterhardiness of 'Zorro' (U.S. Plant Pat. No. 14,130) or 'Meyer' (unpatented) when grown in Kansas (Table 5). 'L1F' has not shown susceptibility to the zoysiagrass mite when tested at Poteet, Tex., where susceptible varieties have shown the coachwhip leaf symptoms of the mite. 'L1F' has shown good turfgrass performance and temperature adaptation when tested as far north as Beltsville, Md., USDA hardiness zone 7a, which would extend the area of adaptation for 'L1F' in a line from northern Maryland across central Tennessee through northern Arkansas through Oklahoma in an East/West line and on a North/South line from Washington D.C., south through Mexico. 'L1F' will be limited only by winter survival in colder regions. 'L1F' is similar to most fine to medium fine textured zoysiagrasses in water use demands as shown in test situations near Poteet, Tex., and will be limited by adequate precipitation in drier to arid regions. 'L1F' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2012-2013.

| Variety | Leaf Stiffness | Length, 2nd youngest crown leaf --cm-- | Width, 2nd youngest crown leaf --mm-- | Leaf Texture Class |
|---|---|---|---|---|
| 'L1F' | Very Soft | 3.02 | 1.60 | Medium Fine |
| 'LR1' | Medium Stiff | 3.67 | 3.27 | Medium |
| 'LR2' | Medium Stiff | 2.96 | 2.61 | Medium |
| 'Diamond' | Soft | 2.50 | 1.40 | Very Fine |
| 'Cavalier' | Medium Stiff | 3.78 | 1.94 | Medium Fine |
| Zorro | Medium Stiff | 4.30 | 1.74 | Medium-Coarse |
| Lsd, p = 0.05 | | 1.03 | 0.24 | |

TABLE 2

Adaxial leaf hair presence or absence of selected zoysiagrass cultivars, measured under greenhouse conditions in Lebanon, OR, 2012-2013.

| Variety | Leaf hair, adaxial Presence/ Number |
|---|---|
| 'L1F' | Absent |
| 'Palisades' | Many |
| 'Zorro' | Many |
| 'Diamond' | Absent |
| 'Royal' | Absent |
| 'Crowne' | Many |
| 'Cavalier' | Many |

TABLE 3

Stolon characters of selected zoysiagrass cultivars, measured under greenhouse conditions in Lebanon, OR, 2012-2013.

| Variety | Thickness 1st youngest stolon node -mm- | Thickness 2nd youngest stolon node -mm- | Stolon Internode length, 1st to 2nd node -cm- | Stolon Internode length, 2nd to 3rd node -cm- | Stolon Internode length, 3rd to 4th node -cm- |
|---|---|---|---|---|---|
| 'L1F' | 1.72 | 1.78 | 1.35 | 1.31 | 1.33 |
| 'Cavalier' | 1.65 | 1.57 | 1.22 | 1.38 | 1.38 |
| 'Diamond' | 1.44 | 1.49 | 1.0 | 0.94 | 1.86 |
| 'Zorro' | 1.57 | 1.67 | 1.51 | 1.47 | 1.45 |
| Lsd, p = 0.05 | 0.16 | 0.38 | 0.34 | 0.28 | 0.31 |

TABLE 4

Leaf and canopy characters of selected zoysiagrass cultivars, measured under greenhouse conditions in Lebanon, OR, 2012-2013.

| Variety | Canopy height --cm-- | Width, 4th youngest crown leaf --mm-- |
|---|---|---|
| 'L1F' | 7.01 | 1.49 |
| 'LR1' | 6.62 | 2.69 |
| 'LR2' | 7.32 | 2.18 |

TABLE 4-continued

Leaf and canopy characters of selected zoysiagrass cultivars, measured under greenhouse conditions in Lebanon, OR, 2012-2013.

| Variety | Canopy height --cm-- | Width, 4th youngest crown leaf --mm-- |
|---|---|---|
| 'Diamond' | 7.24 | 1.15 |
| 'Cavalier' | 10.8 | 1.55 |
| 'Zorro' | 11.09 | 1.41 |
| Lsd, p = 0.05 | 1.76 | 0.71 |

TABLE 5

Characteristics of zoysiagrass from the NTEP trial. Characteristics rated on a scale of 1-9 with 9 = best color or finest texture. Winterkill rated on a scale of 1 to 100, with 100 equal to complete winterkill in Kansas. Mole cricket damage rated 1-9, with 9 = no damage. Diseases rated 1-9, with 9 = no disease.

| | Leaf texture rating | Spring Green-up | Winter-Kill in Kansas | Large brown patch rating (1) | Dollar spot Rating (2) | Mole Cricket Damage (1) |
|---|---|---|---|---|---|---|
| | Year | | | | | |
| Name | 2008 | 2008 | 2008 | 2012 | 2008-12 | 2007-12 |
| 'L1F' | 7.8 | 2.4 | 99 | 7.0 | 6.8 | 6.8 |
| 'Shadowturf' | 7.7 | 2.3 | 99 | 6.5 | 6.9 | 6.5 |
| 'DALZ 0701' | 7.5 | 3.8 | 66.7 | 7.0 | 5.1 | 5.5 |
| 'Dynasty' | 7.4 | 2.7 | 96.3 | • | • | • |
| 'DALZ 0702' | 7.4 | 3.5 | 68.3 | 6.5 | 5.7 | 6.3 |
| 'Zorro' | 7.2 | 4.2 | 14.7 | 5.5 | 6.5 | 6.5 |
| '380-1' | 6.9 | 5.2 | 26.7 | 5.5 | 8.2 | 7.2 |
| 'Meyer' | 5.7 | 5.5 | 0 | 4.5 | 8.6 | 6.3 |
| '240' | 5.3 | 5.3 | 0 | 4.0 | 8.6 | 5.8 |
| '29-2' | 5.3 | 6.4 | 0 | 4.3 | 8.5 | 5.7 |
| 'Zenith' | 4.6 | 5.7 | 5 | 3.5 | 8.7 | 6.5 |
| Lsd, p = 0.05 | 0.3 | 0.6 | 10.6 | 1.3 | 0.8 | 1.6 |

1) Gainesville, FL
2) Raleigh, NC

Origin: 'L1F' is a cultivar of a single clone discovered under cultivated conditions in a Poteet, Tex. planting of zoysiagrass clones derived from a collection of zoysiagrasses from Kobe, Japan made by Jack Murray (deceased).

Classification: *Zoysia japonica* (L.) Merr.

Growth habit: 'L1F' is a perennial plant that spreads by stolons and rhizomes and produces a dense, fine textured turfgrass. The inflorescence of 'L1F' is a terminal spike-like raceme, with spikelets on short pedicels.

Leaf blade: Rolled in the bud, flat surface.

Leaf blade pubescence: No hairs on abaxial or adaxial leaf.

Leaf sheath pubescence: Absent except for long hairs at mouth of sheath.

*'L1F' mean length sheath mouth hairs.*—1.2 mm; Diamond 1.0 mm.

Leaf blade margin: 'L1F'=slight roughness; BM230=rough; Cavalier=mostly smooth.

Leaf blade veins: Prominent.

Leaf blade flexibility (softness): Soft.

Vegetative leaf, 2nd youngest vegetative leaf:

*Blade length range.*—'L1F': 2.7 cm to 4.8 cm, mean length: 3.02 cm.

*Blade width mean.*—'L1F': 1.4 mm to 1.88 mm, mean width: 1.6 mm.

*'Zorro' mean width.*—1.74 mm.

*'Diamond' mean width.*—1.4 mm.

Sheath length, $4^{th}$ youngest vegetative leaf:

*Mean length 'L1F'.*—4.0 cm.

*'Diamond' mean length.*—2.93 cm.

Stolon leaf angle, third youngest leaf: 'L1F': 60; 'Cavalier': 76; 'Diamond': 52.

Inflorescence characters:

*Culm total length, including floral area to node below flag leaf.*—24.3 mm. Length of stem of inflorescence: 14.3 mm. Floral area length: 10.7 mm.

*Culm width, stem thickness, base of floral area.*—0.77 mm.

*Anther length.*—1.0 mm. $1^{st}$ Glume: Lacking. $2^{nd}$ glume width: 0.6 mm. $2^{nd}$ glume length: 3.5 mm.

*Spikelet number per inflorescence.*—12.8.

*Spikelet length.*—3.2 mm.

*Spikelet width.*—0.4 mm; Note that the spikelet is only slightly smaller than the $2^{nd}$ glume because the $2^{nd}$ glume enfolds the lemma with the palea apparently absent.

*Peduncle width.*—0.5 mm.

*Peduncle length.*—29.3 mm.

*Node thickness, node below flag leaf.*—0.75 mm.

*Pedicel length.*—2.0 mm.

*Flag leaf length.*—'L1F': 15.0 mm.

*Flag leaf width.*—'L1F': 1.0 mm.

Inflorescence emergence: 'L1F' has sparse flowering in Poteet, Tex. from late April through October.

Mature plant height, including inflorescence: 6 to 7 cm.

Color notations, vegetative characters, based on The R.H.S. Colour Chart, 2001 (light quality, photoperiod, and general growth of the plants affect color notations):

*Leaf blade color adaxial leaf surface.*—138A green.

*Leaf blade color abaxial leaf surface.*—138A green.

*Stolon color.*—161C, 161A greyed yellow.

Color notations, floral characters, based on The R.H.S. Colour Chart (light quality, photoperiod, and general growth of the plants affect color notations):

*Culm stalk.*—145C yellow green.

*Stigma.*—155B white.

*Anther color, fresh.*—155A white.

*Anthers, mature, dried.*—158B yellow-white.

Turf quality (rated 1-9, 9 best): 'L1F': 6; 'Meyer': 5.

*Stolon density.*—Similar to Diamond (U.S. Plant Pat. No. 10,636); more than Cavalier (U.S. Plant Pat. No. 10,778).

I claim:

1. A new and distinct variety of zoysiagrass plant, substantially as described and illustrated herein, characterized particularly by a unique combination of morphological characters.

* * * * *

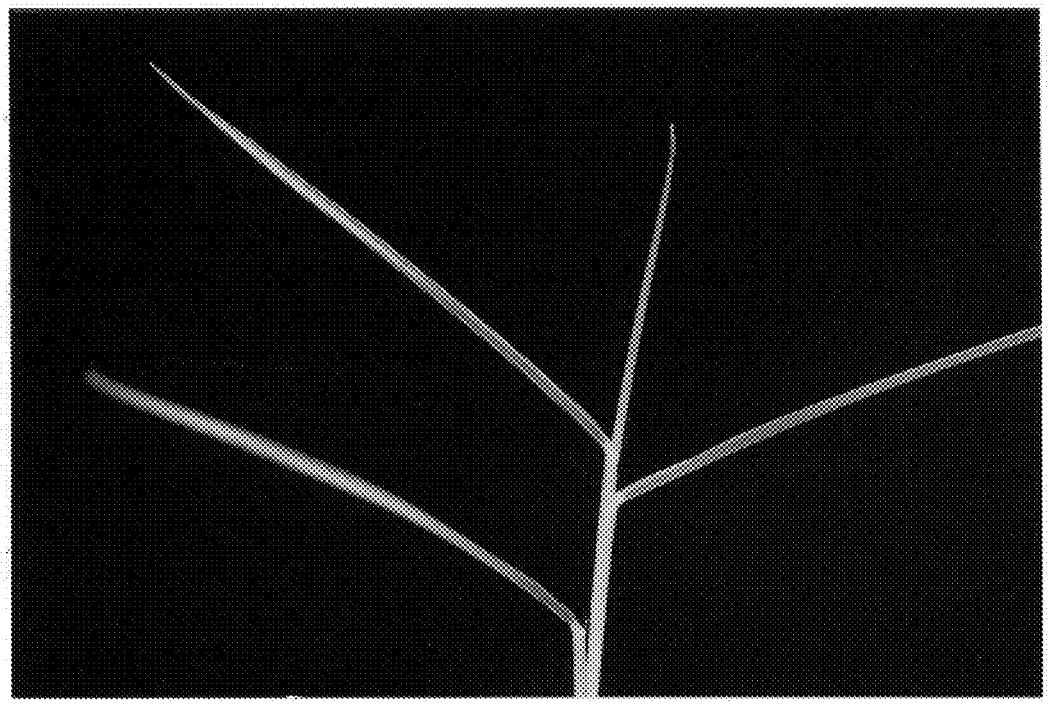
Figure 1. Tiller of 'L1F' zoysiagrass.

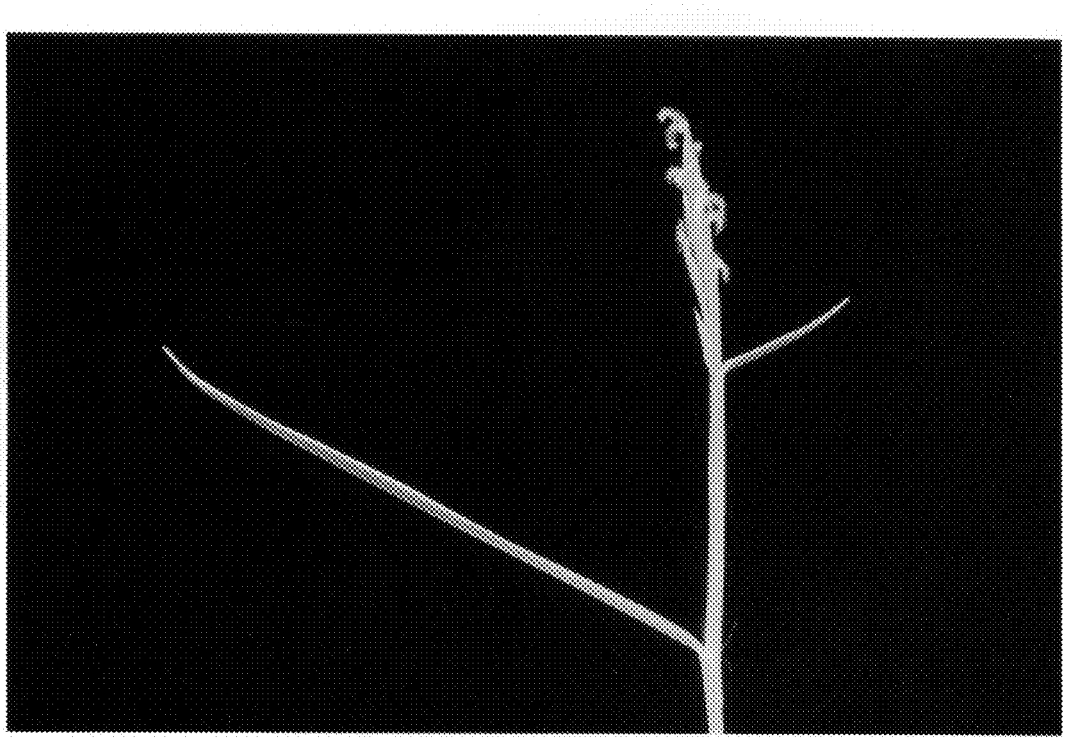
Figure 2. Inflorescence of 'L1F' zoysiagrass.